United States Patent

McDonald et al.

[11] Patent Number: 6,090,136
[45] Date of Patent: Jul. 18, 2000

[54] SELF EXPANDABLE TUBULAR SUPPORT

[75] Inventors: Edward A. McDonald, Irvine; Joe W. Young, Laguna Niguel; Michael Henson, Trabuco Canyon, all of Calif.

[73] Assignee: Radiance Medical Systems, Inc., Irvine, Calif.

[21] Appl. No.: 08/881,956

[22] Filed: Jun. 25, 1997

Related U.S. Application Data

[63] Continuation-in-part of application No. 08/754,816, Nov. 21, 1996, Pat. No. 5,728,150, which is a continuation-in-part of application No. 08/681,906, Jul. 29, 1996, Pat. No. 5,676,697.

[51] Int. Cl.[7] ........................................... A61F 2/00
[52] U.S. Cl. ............................................. 623/1.23
[58] Field of Search ................... 623/1, 11, 12, 623/1.23; 606/194, 195

[56] References Cited

U.S. PATENT DOCUMENTS

| | | |
|---|---|---|
| Re. 34,327 | 7/1993 | Kreamer . |
| 4,665,918 | 5/1987 | Garza et al. . |
| 4,739,762 | 4/1988 | Palmaz . |
| 4,740,207 | 4/1988 | Kreamer . |
| 4,776,337 | 10/1988 | Palmaz . |
| 4,800,882 | 1/1989 | Gianturco . |
| 4,877,030 | 10/1989 | Beck et al. . |
| 4,922,905 | 5/1990 | Strecker . |
| 5,007,926 | 4/1991 | Derbyshire . |
| 5,059,211 | 10/1991 | Stack et al. . |
| 5,078,726 | 1/1992 | Kreamer . |
| 5,089,006 | 2/1992 | Stiles . |
| 5,100,429 | 3/1992 | Sinofsky et al. . |
| 5,167,614 | 12/1992 | Tessmann et al. . |
| 5,171,262 | 12/1992 | MacGregor . |
| 5,192,307 | 3/1993 | Wall . |
| 5,234,448 | 8/1993 | Wholey et al. . |
| 5,242,399 | 9/1993 | Lau et al. . |
| 5,254,127 | 10/1993 | Wholey et al. . |
| 5,266,073 | 11/1993 | Wall . |
| 5,306,286 | 4/1994 | Stack et al. . |
| 5,306,294 | 4/1994 | Winston et al. . |
| 5,344,426 | 9/1994 | Lau et al. . |
| 5,354,309 | 10/1994 | Schnepp-Pesch et al. . |
| 5,366,473 | 11/1994 | Winston et al. . |
| 5,383,926 | 1/1995 | Lock et al. . |

(List continued on next page.)

OTHER PUBLICATIONS

Scanning Electron Microscopy Evaluation of Porous and Nonporous Arterial Substitutes, Giovanni B. Ratto, M.D., Carmen Lunghi, M.D., Enzo Spinelli, M.D., Marzia Tomellini, M.D., and Giovanni Motta, M.D., Genoa, Italy, Surgery, *Gynecology & Obstetrics*, Sep. 1982, vol. 155.

Morphology of Healing in Vascular Prosthesis, G. Rahlf, P. Urban, and R.M. Bohle, Read at the 14th Annual Meeting of the German Society for Thoracic and Cardiovascular Surgery, Bad Nauheim 1985, *Thoracic Cardiovascular Surgeon* 34 (1986).

Endothelial Cell Adhesion to Vacular Prosthetic Surfaces, D. Gourevitch, Carolyn E. Jones, J. Crocker and M. Goldman, Presented at Biointeractions '87, Cambridge, UK in Jul. 1987, Biomaterials 1988, vol. 9, Jan.

Restenosis After Balloon Angioplasty, A Practical Proliferative Model in Porcine Coronary Arteries, Robert S. Schwartz, MD, Joseph G. Murphy, MB, William D. Edwards, MD, Allan R. Camrud, RN, Ronald Vlietstra, MB, BCh. and David R. Holmes, MD, *Circulation* vol. 82, No. 6, Dec. 1990.

*Primary Examiner*—Michael J. Milano
*Attorney, Agent, or Firm*—Knobbe, Martens, Olson & Bear, LLP

[57] ABSTRACT

Disclosed is a tubular prosthesis formed by rolling a flexible sheet around a longitudinal axis. Preferably, the prosthesis is self expandable under the radially outwardly directed spring bias of the rolled sheet. Also disclosed are catheters for delivering two or more of the tubular prostheses at a site within a body lumen. Multiple prostheses may be deployed directly against a vessel wall in a single procedure, or may be deployed within a vascular graft to provide support throughout the length of the graft.

23 Claims, 6 Drawing Sheets

U.S. PATENT DOCUMENTS

| | | |
|---|---|---|
| 5,405,379 | 4/1995 | Lane . |
| 5,411,549 | 5/1995 | Peters . |
| 5,411,551 | 5/1995 | Winston et al. . |
| 5,423,885 | 6/1995 | Williams . |
| 5,441,515 | 8/1995 | Khosravi et al. . |
| 5,443,500 | 8/1995 | Sigwart . |
| 5,449,382 | 9/1995 | Dayton . |
| 5,540,713 | 7/1996 | Schnepp-Pesch et al. . |
| 5,578,075 | 11/1996 | Dayton .................................... 623/1 |
| 5,707,385 | 1/1998 | Williams .................................... 623/1 |
| 5,723,003 | 3/1998 | Winston et al. . |
| 5,766,710 | 6/1998 | Turnlund .................................... 623/1 |

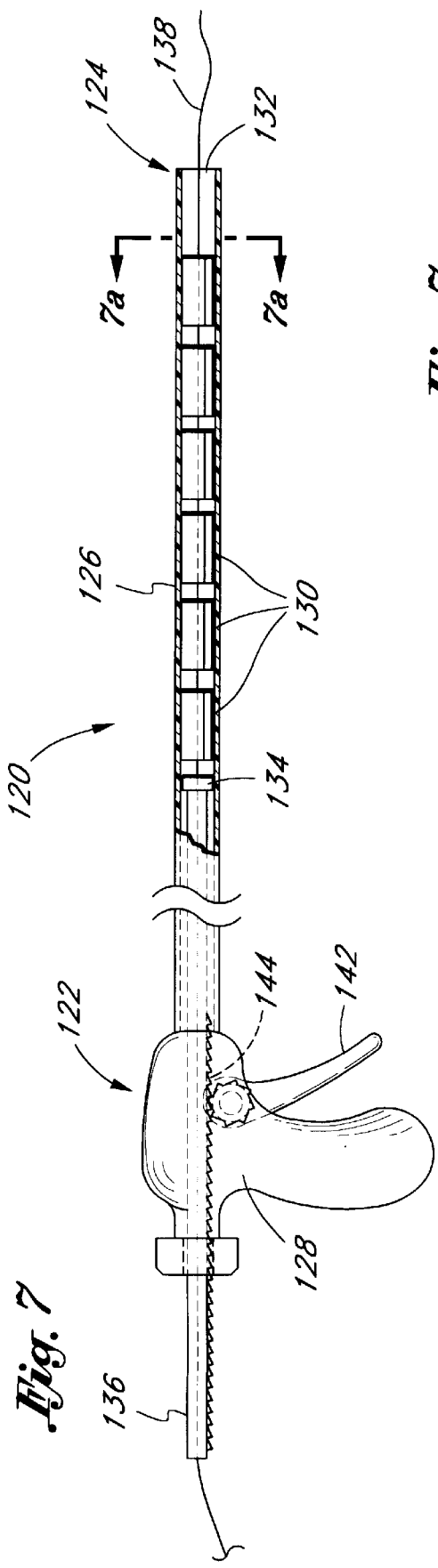
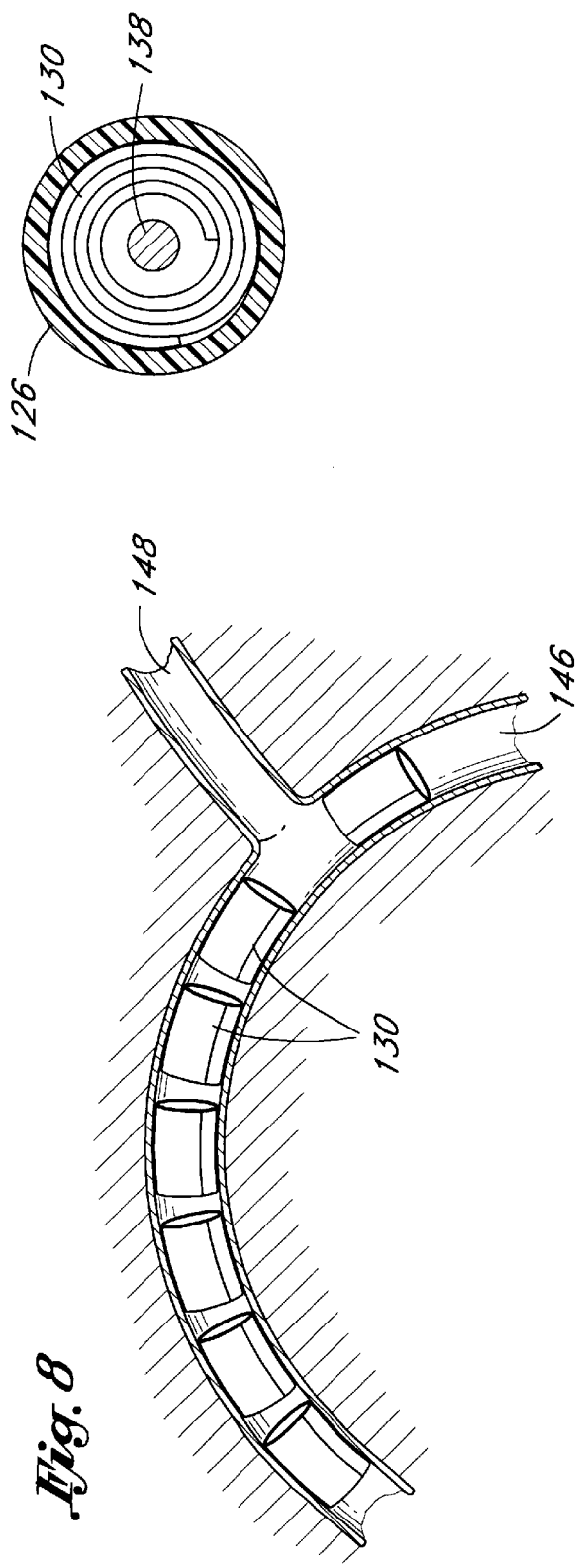

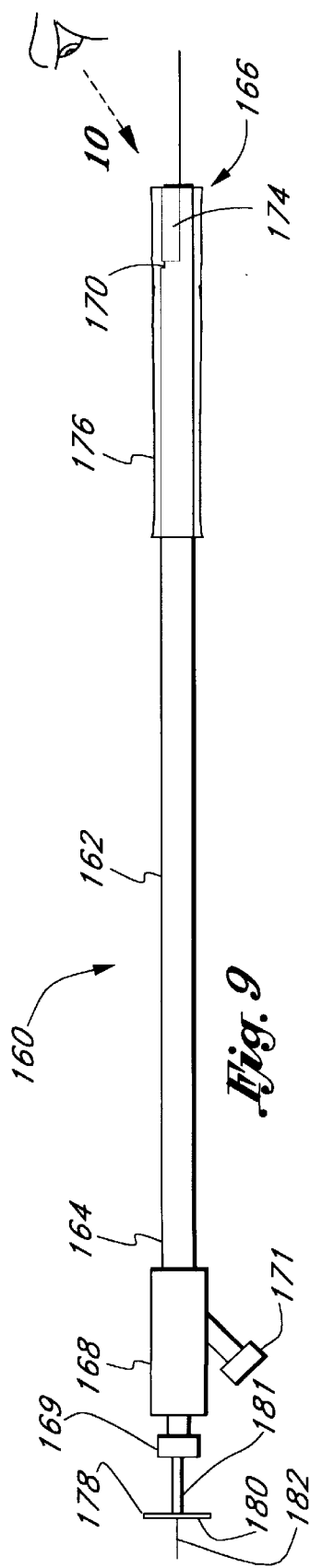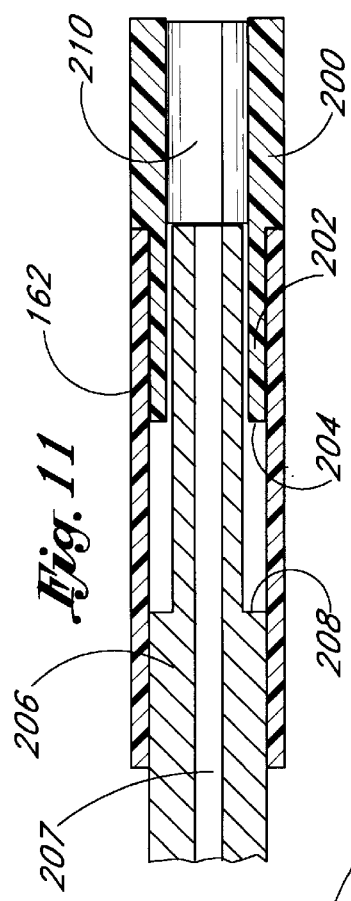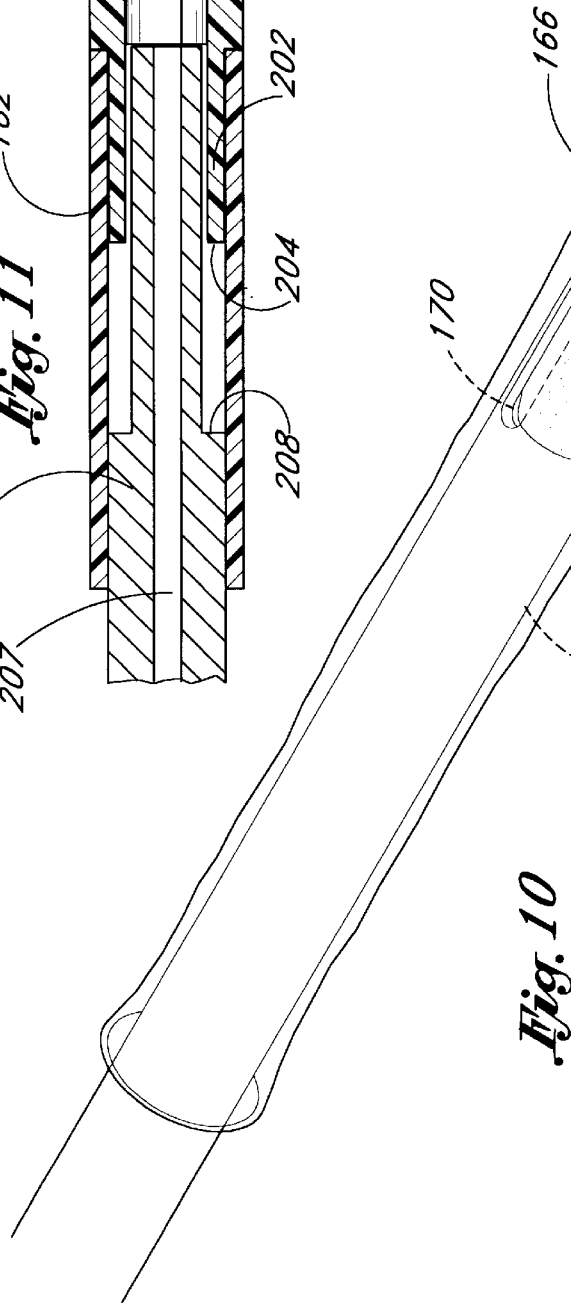

SELF EXPANDABLE TUBULAR SUPPORT

CROSS-REFERENCE TO RELATED APPLICATION

This is a continuation-in-part of commonly assigned, U.S. patent application Ser. No. 08/754,816 filed Nov. 21, 1996, now U.S. Pat. No. 5,728,150, which is a continuation-in-part of U.S. patent application Ser. No. 08/681,906 filed Jul. 29, 1996, now U.S. Pat. No. 5,676,697.

FIELD OF THE INVENTION

The present invention relates to intraluminal stents and grafts that are adapted to be advanced in a collapsed roll to the site of an aneurysm, defect or injury of a body vessel and expanded or allowed to self expand across the site.

BACKGROUND OF THE INVENTION

In numerous medical and surgical techniques, stents, grafts, or stent-grafts hereinafter sometimes referred to as implantable tubular prostheses, are inserted into body vessels or ducts or the like, temporarily or permanently, in order to repair a defect or maintain the patency of the vessel or duct lumen to as great a degree as possible. Transluminal implantation of such prostheses requires that they be introduced to the site collapsed about or within an introduction device and released to self expand or are expanded by other mechanisms to an expanded tubular state providing a lumen of approximately the same size as the patent vessel or duct lumen.

A wide variety of such tubular prostheses have been proposed for introduction through a percutaneous access site and advancement through the vascular system to an aneurysm, defect or injury site and for deployment to bridge the site. Once deployed in situ, the prosthesis must be stabilized mechanically until neointimal growth occurs over the graft ends and interior surface. Such prostheses have been formed of a wide variety of materials and shapes to accommodate particular vascular sites and to encourage neointimal growth. In addition, a wide variety of deployment mechanisms and techniques have been proposed to position and stabilize the prosthesis in place including "active" fixation mechanisms designed to penetrate the vessel wall and "passive" fixation mechanisms that press against and expand the diameter of the vessel lumen.

For example, certain expandable metal "wire stents" have been employed in clinical use for insertion into an artery in order to assist in preventing re-stenosis after a balloon angioplasty procedure has been completed to expand a stenosed site. These wire stents are relatively structurally stiff, and when expanded at the site (typically by a further balloon catheter) engage the previously (or simultaneously) compressed remnant of the occlusion in the vessel and are passively retained in place by friction until neointimal growth permanently encases the stent. Typically, such wire stents are formed of wire mesh or wire loops or are formed of a perforated metal sheet, as shown, for example, in U.S. Pat. Nos. 4,776,337, 4,877,030, 5,007,926, and 5,079,006. Such wire stents have relatively large openings in the side wall thereof in relation to the wire gauge or remaining sheet material bounding the openings. After insertion to the site of implantation, the inner diameter of the tubular wire stent can be expanded by a balloon catheter or the like into engagement with the vessel wall. The large openings result from the attempt to minimize the number of wire strands and turns of the stent, because, after expansion in situ, each exposed turn or strand slightly intrudes into the vessel lumen and causes perturbation in the blood flow and can constitute a site of formation of blood clots. In addition, the expandable wire or sheet stents must expand to achieve their objective and therefore by design must leave open spaces. The more they expand, the more open space they must leave.

Such wire stents are formed of a single layer of wire mesh or strand in either a tubular form or a rolled sheet form. When the rolled sheet form is expanded, only a minor overlap if any of adjoining edges is contemplated as shown in the structures shown in the '030, '006 and '926 patents. The resulting stent structure is porous, but blood flow through the openings between wire turns or through the perforations is not an issue because the openings or perforations bear against the vessel wall. The blood contact or circulation alongside the openings or perforations encourages neointimal ingrowth to stabilize the stent. However, the relatively large openings can also allow fibrotic build-up to occur through the openings and possibly constrict the wire stent lumen over time. In addition, the relatively large openings are not very effective in repairing other defects in the vessel wall, e.g., a tear or dissection, thus limiting the uses of such stents.

At this point, it should be pointed out that at times, the term "stent" is used interchangeably in the prior art with "graft," although vascular grafts classically are longer and have less porous side walls than the above-described wire stent. The expression "vascular graft" originally was used to described harvested blood vessels used to bypass a length of diseased or enlarged blood vessel, and the expression "artificial graft" typically connotes an elongated, biocompatible, tubular body mimicking the flexibility of the natural blood vessel it is intended to replace. In an open chest surgical procedure, the active attachment of such flexible vascular or artificial grafts to patent blood vessel ends is effected by suturing in a procedure referred to as anastomosis.

Elongated, artificial "intraluminal grafts" have also been developed for use in an intraluminal implantation procedure to bridge elongated aneurysms, defects or injuries to avoid invasive vascular surgery. Such intraluminal grafts are typically formed of a single tube of flexible biocompatible materials, e.g., a Dacron fabric tube that is long enough or shaped especially to bridge the defective region of the blood vessel, coupled with one or more retention mechanism at an end or ends thereof. Certain of the retention mechanisms proposed for use with such intraluminal grafts employ passive stents at each end that are allowed to self expand or are expanded to enlarge and frictionally engage patent vessel wall on either side of the site as shown, for example, in U.S. Pat. No. 3,991,767. The end stents may alternatively include active barbs or hooks that are manipulated to invade the patent vessel wall and retain the graft in position. Such combinations of stent and graft structures are at times referred to as "stent-grafts" and are also shown, for example, in U.S. Pat. Nos. 5,078,726 and 5,336,473.

Another artificial intraluminal stent that is typically not porous and may be used to bridge a defect or maintain the patency of an expanded vessel lumen is formed as a tubular body from a sheet of biocompatible metal, plastic or other material. The sheet metal is rolled up in a collapsed roll state in one or more overlapping layers that can be advanced intraluminally and expanded to bridge the site. Examples of such intraluminal stents and introduction systems are shown, for example, in U.S. Pat. Nos. 34,327, 4,740,207, 5,100,429, 5,306,294 and 5,405,379. Such stents are also employed as the end fixation mechanisms in stent-grafts as shown in certain embodiments of the above-referenced '726 and '473 patents.

The stents disclosed in the above-referenced '473 and '294 patents are advantageous in that they are formed of a sheet of metal foil adapted to be rolled into a plurality of sheet layers forming the collapsed and expanded rolls that are radiopaque and allow visualization of their advancement and deployment at the site. Moreover, when released at the site, no separate expansion mechanism is required because the rolled up sheet material self expands to a size that fits and slightly expands the lumen of the vessel or duct. The stent or stent-graft is retained by passive engagement of the expanded roll of sheet material against the vessel or duct lumen caused by the expansion spring force tending to further expand the diameter of the expanded tubular member. As a result of the self expansion spring force and the expansion range, sizing of the expanded tubular body diameter to the vessel or duct lumen is not critical. The multiple overlapping layers ensure that no gap can occur between the opposite edges of the sheet. Moreover, the rolled, overlapping layers forming the side wall of the stent provides substantial hoop strength to resist or prevent re-stenosis in the vessel wall. Certain of these advantages are also obtained by the nonradiopaque stent depicted in the above-referenced '579 patent.

In such self expanding (or balloon expandable) multiple layer side wall stents formed of rolled sheet material as described in the above-referenced patents, the nonporous smooth inner lumen advantageously does not create flow perturbations along its length. On the other hand, the impervious side wall formed by the roll of sheet material is likely to limit the area of neointimal growth within the stent lumen to about 0.125 inches from each end opening. Consequently, over a period of days or weeks, blood clots may be encouraged to form by contact with the exposed sheet material of the inner lumen surface. The blood clots can break away and migrate to a site posing a danger to the patient. It may therefore be necessary to suppress clot formation with anticoagulant drugs, e.g., coumarin, aspirin, or others, for extended indefinite periods of time in the case of solid sheet material stents.

Notwithstanding the foregoing, there remains a need for a stent design with sufficient hoop strength and structure for permitting neointimal tissue ingrowth, as well as the capability to treat vascular sites which may extend along curved portions of the vessel. In addition, there remains a need for grafts which can be readily implanted, are flexible to track curved portions of the vessel, and which provide sufficient support to maintain patency.

SUMMARY OF THE INVENTION

There is provided in accordance with one aspect of the present invention an intravascular graft delivery catheter. The catheter comprises an elongate flexible tubular body, having a self-expanding graft support removably positioned within the tubular body. An elongate flexible tubular graft is secured to the graft support, and extends proximally along the tubular body.

In one embodiment, the graft support extends proximally along the outside of the tubular body, and the tubular body and graft support are further positioned within an outer introduction sheath. Preferably, at least a second graft support is movably positioned within the tubular body.

In accordance with another aspect of the present invention, there is provided an endobypass delivery system. This system comprises an elongate flexible tubular body having a sidewall and a proximal end and a distal end. A support cavity is provided in the tubular body, accessible through both an end opening on the distal end of the tubular body and through a side opening in the sidewall of the tubular body.

A first self-expanding support is positioned in the support cavity, the support having a free edge extending through the side opening. A tubular graft is attached to the free edge and extends proximally along the tubular body.

Preferably, the self-expanding support comprises a flexible sheet rolled into a tubular configuration. The system preferably further comprises an elongate flexible deployment column, extending axially through the tubular body, for deploying the self-expanding support. At least a second, and, in some embodiments, at least a third or fourth or more additional self-expanding supports are positioned in the support cavity, for providing intermediate support between the ends of the tubular graft.

In accordance with another aspect of the present invention, there is provided an elongate flexible tubular graft. The graft comprises a flexible tubular graft body, having a proximal end, a distal end and a central lumen extending there through. A distal self-expanding graft support is positioned within the distal end of the graft, and a proximal self-expanding graft support is positioned within the proximal end of the graft. At least one intermediate self-expanding support is positioned within the graft between the distal support and the proximal support. Preferably, at least two or three or more intermediate supports are positioned within the graft between the distal support and the proximal support. In one embodiment, the distal self-expanding support is attached to the graft.

In accordance with a further aspect of the present invention, there is provided a method of implanting a graft. The method comprises the steps of providing a delivery catheter having a graft and at least a first and a second self-expanding tubular supports thereon. A distal end of the graft is advanced to a site within a body lumen, and a first support is deployed to secure the distal end of the graft at the site. The catheter is retracted proximally within the graft, and a second support is deployed to secure the proximal end of the graft at the site. Preferably, at least a third support is deployed in between the first and second supports. In an alternative method, at least one support is positioned within the graft. The delivery catheter is then advanced distally to deploy at least a second support within the graft. Thus, depending upon the procedure, two or more supports can be introduced into a graft or vessel in either a distal to proximal or a proximal to distal direction.

In one application, the method comprises advancing a distal end of the graft through the femoral artery. In another application, the advancing a distal end of the graft step is accomplished through the aorta.

In accordance with a further aspect of the present invention, there is provided a method of deploying multiple supports (stents) within a vessel. The multiple supports may be deployed directly against the vessel wall, such as following PTCA or PTA, or within a previously implanted graft.

The method comprises the steps of providing an elongate flexible tubular support delivery catheter, having a support lumen with a plurality of supports therein. The catheter is positioned at a site within a body lumen, and a first set of at least one support is deployed at the site. The catheter is moved axially proximally or distally within the site, and a second set of at least one support is deployed within the site. The treatment site may have an axial length within the range of from about 2 cm to about 40 cm.

In accordance with a further aspect of the present invention, there is provided a method of providing intermediate support along the length of a vascular graft. The method comprises the steps of providing a support delivery catheter having a plurality of self-expanding supports. The support delivery catheter is positioned within a distal portion of a vascular graft, and a first support is dispensed within the distal portion of the vascular graft. The catheter is thereafter retracted proximally, and at least a second and a third self-expanding supports are deployed within the graft spaced axially apart in the proximal direction relative to the first support.

In accordance with a further aspect of the present invention, there is provided a stent delivery catheter for delivering multiple stents to a site within a body lumen. The catheter comprises an elongate flexible tubular body, having a proximal end and a distal end and a central lumen extending axially there through. At least two self-expandable tubular stents are positioned in the lumen, the stents enlargable from a first, reduced diameter to a second, enlarged diameter upon release from the catheter. An elongate flexible deployment core extends through the catheter for deploying the tubular stents from the catheter. Preferably, at least as many as three or five or more self-expanding tubular stents are provided in the lumen.

In accordance with a further aspect of the present invention, there is provided a method of introducing multiple self-expanding stents within a lumen. The method comprises the steps of providing an elongate flexible tubular deployment catheter having a stent lumen extending axially throughout at least a distal portion thereof, and an axially moveable stent deployment core positioned within at least a proximal portion of the stent lumen. The catheter is transluminally advanced through a vessel to a treatment site. The deployment core is thereafter held in a fixed axial position within the lumen. The catheter is proximally retracted relative to the core, and the axially fixed core causes at least a second stent to be deployed within the lumen.

These and other advantages and features of the invention will become apparent from the following detailed description of the preferred embodiments of the invention.

BRIEF DESCRIPTION OF THE DRAWINGS

FIG. 7 is a side elevational schematic illustration of a multiple stent deployment tool in accordance with another aspect of the present invention.

FIG. 7a is a cross-sectional view through the line 7a—7a in FIG. 7.

FIG. 8 is a schematic view of a plurality of stents of the present invention implanted within a curved vessel.

FIG. 9 is a side elevational schematic view of a stent graft deployment tool in accordance with another aspect of the present invention.

FIG. 10 is a perspective view of a distal portion of the deployment tool of FIG. 9.

FIG. 11 is a cross-sectional view through the distal end of an alternate stent graft deployment tool.

Figure 1:
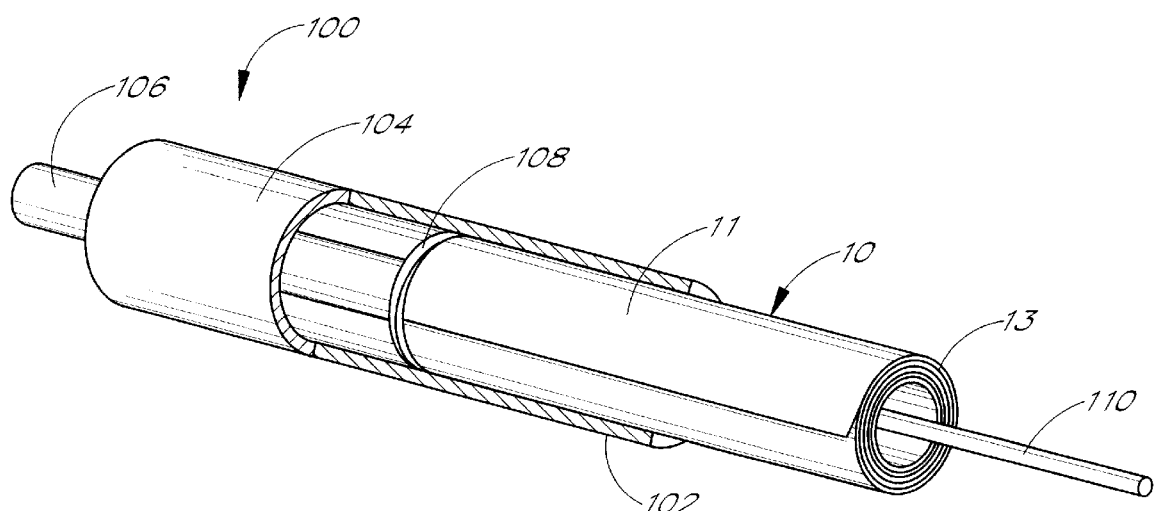
FIG. 1 is a fragmentary perspective view of a stent in accordance with the present invention and the distal end of one exemplary form of a placement system for placing the stent in its collapsed roll state at a desired site in a body lumen.

The drawing figures are not necessarily to scale.

DETAILED DESCRIPTION OF PREFERRED EMBODIMENTS

The present invention is described in the context of an embodiment of a tubular graft for intraluminally bridging an aneurysm, defect or injury or for supporting and maintaining a vessel lumen at the site of a stenotic lesion from re-stenosis following an angioplasty or other procedure for opening a blood vessel lumen. It will be understood that the invention may be incorporated into prostheses of all types for maintaining patency of lumens of blood vessels or other body ducts or vessels and that the expression "body lumen" includes all such lumens.

Turning to FIG. 1, it depicts a prosthesis 10 constructed in accordance with a preferred embodiment of the invention in relation to an exemplary stent placement system 100 that may be used to intraluminally introduce and release the stent 10 at a desired body site. Alternate deployment systems and useful deployment methods are disclosed in U.S. Pat. Nos. 5,405,379; 5,306,294 and 5,336,473, the disclosures of which are incorporated herein by reference.

The stent 10 is shown in its retracted state and partially deployed from the distal end 102 of a tubular introducer catheter 104. The illustrated introducer catheter 104 has an inside diameter substantially equal to the outer diameter of the stent 10 when in its collapsed roll state. The catheter 104 is provided with at least one elongate lumen extending axially therethrough, for removably receiving a central core or pusher 106. In the illustrated embodiment, pusher 106 comprises an elongate flexible tubular element having an outside diameter which is less than the inside diameter of the catheter 104. The pusher 106 is therefore preferably provided with a stop 108 on the distal end thereof for permitting the pusher 106 to efficiently push at least one prosthesis 10 distally from the catheter 104. In use, the pusher 106 will generally be held in an axially fixed position and the catheter proximally withdrawn to deploy the prosthesis 10, as will be discussed below. Preferably, the catheter 104 is adapted to be introduced over a guidewire 110, which is axially slidably received through the coiled prosthesis 10 and through the lumen within pusher element 106.

As shown in FIG. 1, the prosthesis or stent 10 is formed of a sheet 11 that is rolled up into a tubular body 13 of multiple overlapping layers of sheet 11. The tubular body 13 therefore has a side wall formed of the multiple rolled up layers of sheet 11, an inner lumen around the guide wire 110, and an axial length extending, in the longitudinal direction of the introducer catheters 104 between proximal and distal tubular body ends. The proximal tubular body end butts against the stop 108, and the distal tubular body end will generally be positioned near the distal end 102 of catheter 104. The guide wire 110 guides introduction of the distal end 102 of the outer introducer catheter 104 including the stent 10 within it to a body lumen site for deployment of the stent 10 in a manner generally taught in the above-referenced '294 and '473 patents, incorporated herein by reference in their entireties.

The reduced implantation diameter of the tubular body 13 is dictated by the inside diameter of the catheter 104. In an alternative embodiment of the placement system 100 such as that disclosed in the '294 patent, the outer sheath 104 is not used and cords (not shown in FIG. 1) are used to restrain the sheet 11 in the collapsed roll state until the cords are withdrawn all in a manner taught in the above-incorporated '294 patents.

In accordance with a method of installation using the depicted placement system 100, the perforated sheet 11 is rolled up into a tubular stent 13 such as by rolling the sheet 11 around a mandril (not illustrated). The rolled tubular body 13 is then loaded into the distal end 102 of the introduction catheter 104, either at a point of manufacture, or at the clinical site. The radially outwardly directed bias of the tubular body 13, as discussed in greater detail infra, causes the tubular body 13 to press radially outwardly against the interior wall of the catheter 104, thereby retaining the tubular body 13 in position within the catheter 104. The introducer catheter 104 and the stent 10 are thereafter introduced over the guide wire 110 and advanced transluminally to the desired body lumen site with the tubular body 13 restrained in the collapsed roll state. At the site, the pusher 106 is advanced distally with respect to the catheter 104 to expel the stent 10 out of the distal end opening of catheter 104. Preferably, the catheter 104 is withdrawn proximally while the pusher 106 is maintained stationary in the vessel. The released tubular body 13 self expands in diameter to its expanded roll state constrained in size by the diameter of the body lumen at the site.

The placement system 100 of FIG. 1 and the method of placement described above provide one example of a system and method for collapsing the stent 10 and for effecting its introduction and release at the site that may be employed with the improved stent 10 of the present invention. Any of a variety of alternate deployment systems can also be used as will be apparent to persons of skill in the art in view of the disclosure herein.

Moreover, the perforation pattern of the stent sheet of the present invention may be incorporated into stents that are not self expanding and are expanded at the site by expansion mechanisms. In such a case, the stent expanded roll state would still have multiple layers of the sheet in the side wall thereof as shown in the remaining figures.

Returning to FIGS. 1–3, the tubular body 13 is formed of a sheet 11 of biocompatible material rolled into a plurality of layers to form the side wall and a central lumen. The tubular body 13 therefore presents a plurality of adjacent arcuate layers of the sheet 11 rolled up in a direction transverse to the longitudinal direction and the longitudinal axis of the stent 10. The sheet 11 possesses an inherent resilience and spring force that seeks to unwind the wound layers and expand the stent lumen as described in the above-incorporated '294 patent, for example. In the fully expanded roll state of the illustrated preferred embodiment within a vessel, there are at least two to three fully overlapping layers that bear against one another under the spring force.

Figure 2:
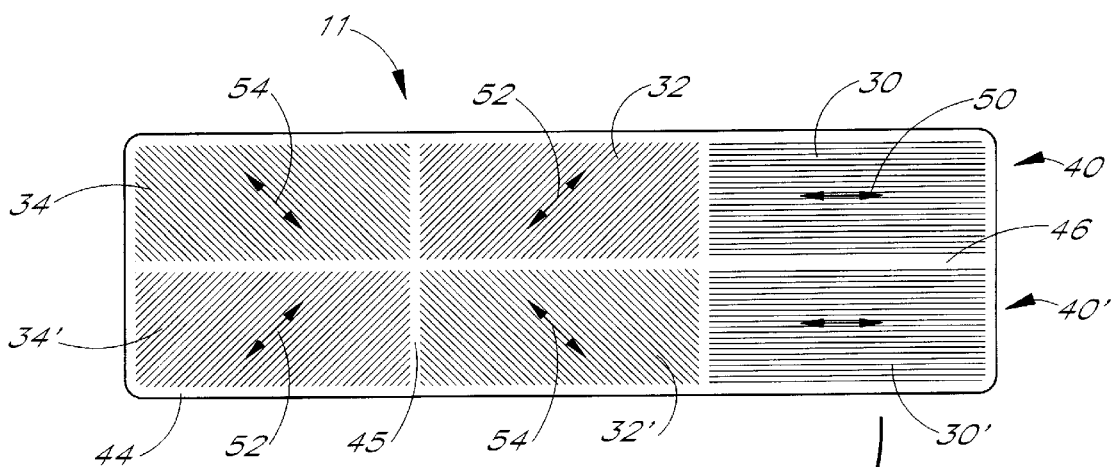
FIG. 2 is a plan view of one sheet pattern from which the stent of the present invention is formed showing the symmetrical orientation of a pair of first, second and third zones of the sheet containing elongated perforations orientated at complementary angles to one another.
Figure 3:
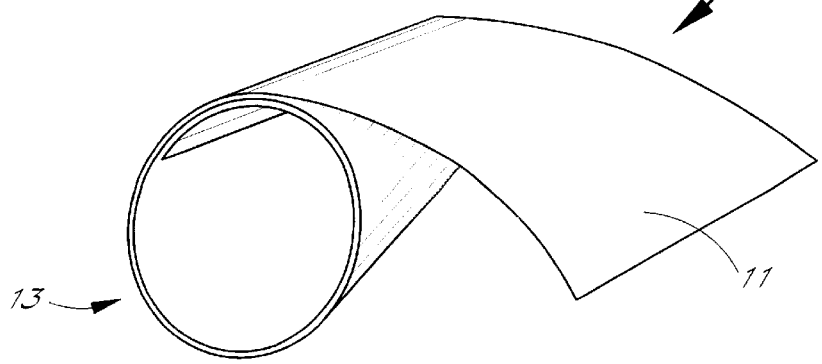
FIG. 3 is a schematic illustration of the sheet of FIG. 2 being rolled into a tubular prosthesis.

Turning to FIG. 2, the sheet 11 is shown flattened out to illustrate the perforation pattern employed in a preferred embodiment of the present invention to assure that openings extend through the multiple layers of the rolled up sheet 11 forming the tubular body 13 in the expanded roll state. The sheet 11 has a sheet length SL providing the plurality of overlapping layers when the sheet 11 is rolled up in the length direction and a sheet width SW corresponding to the axial length of tubular body 13. The sheet width SW and length SL in one 3 cm embodiment are on the order of about 30.0 mm and 116.0 mm, respectively, resulting in a tubular body length of about 30 mm. The sheet 11 may be formed of a biocompatible metal alloy, e.g., Elgiloy, in a foil of a thickness of about 0.0015 inches (about 0.038 mm).

It is contemplated that a sheet 11 having an SL of 116 mm and thickness of about 0.0015 inches may be wound into a collapsed roll state to fit within an introducer sheath lumen of about 3.9 mm in inside diameter and have an inner diameter of about 1.3 mm, in which the number of layers in the tubular member side wall approaches 18. When released in situ, the outer diameter of the tubular member 13 may expand to between 12 mm and 18 mm, resulting in between 3 and 2 layers, respectively, forming the side wall of tubular member 13.

In general, the length of the tubular body 13 (which will normally equal the sheet width of the sheet 11) is selected to optimize performance of the prosthesis in the intended use environment. For example, in an application where the prosthesis is intended to be used as a graft for treating a tubular abdominal aortic aneurysm, the sheet width will generally be within the range of from about 300 mm to about 1000 mm. Preferably, the sheet width is selected to provide a graft having an axial length which is greater than the length of the aneurysm or other diseased site being treated. Preferably, each of the proximal and distal ends of the graft will overlap with healthy vessel for a distance of at least about 10 mm. A relatively greater overlap, such as on the order of 20 mm or greater, may be desirable in straight sections of the aorta, to optimize anchoring and tacking down of the ends of the graft by way of neointimal growth.

The illustrated sheet 11 is provided with a plurality of perforation zones 30, 32, 34 and 30', 32' and 34', arranged in first, second and third positions in first and second mirror image halves 40 and 40', respectively, spaced apart along sheet length SL as shown in FIG. 2. In effect, the perforation zones 30, 32, and 34 are arranged in respective first, second and third portions of the strip in a first row in the first half 40, and the perforation zones 30', 32' and 34' are arranged in respective first, second and third portions of the strip in a second row in the second half 40'. A plurality of elongated perforations 28 (shown in FIG. 6) are formed in each of the generally rectangular perforation zones 30, 32, 34, 30', 32' and 34'. Thus, each line in the parallel interior groups of lines in FIG. 2 represents a row of end-to-end perforations such as those illustrated in an enlarged fashion in FIG. 6.

The first perforation zones 30, 30' are each formed with a first plurality of elongated perforations 28 extending in parallel with one another in a first direction 50 parallel to the longitudinal axis of the sheet 11 and nominally designated as 0°. The second perforation zones 32 and 32' are each formed with a second plurality of elongated perforations 28 extending in second and third directions 52 and 54, respectively, at +45° and −45°, respectively, to the longitudinal axis (the 0° direction 50). The third perforation zones 34 and 34' are formed with a third plurality of elongated perforations 28 extending at 90° to one another in the directions 54 and 52 respectively. In this manner, the perforations 28 in the adjacent perforation zones 32, 32' and 34, 34' are at an angle of 90° to one another and equalize bias forces that arise from the perforation directions 52 and 54 that would tend to cause the sheet 11 to twist when rolled up in the collapsed roll state or as the prosthesis expands to the expanded roll state. Other angles besides 90° may also be used, as long as the longitudinal axes of the elongated perforations are generally symmetric (opposing) across the longitudinal axis to cancel roll bias.

In the illustrated embodiment, each of the three rectangular perforation zones 30, 32, 34 and 30', 32' 34' of the first and second halves 40, 40' are of equal size. The widths of each perforation zones are somewhat smaller than one half the sheet width SW allowing for border and center bands of sheet material. The lengths of each perforation zone along the sheet length SL are substantially the same and are chosen in this case to substantially correspond to the chosen or target circumference of the resulting tubular body in the expanded roll state having substantially three overlapping layers.

The perforation zones 30, 32, 34 and 30', 32' 34' of the first and second halves 40, 40' are formed inside an edge border band 44 extending all the way around the edge of sheet 11 having a width of about 1.2 or 1.3 mm. Similarly, the adjacent perforation zones in each half 40 and 40' are separated from one another by side border bands 45 having a width of about 1.2 mm–1.3 mm. A center border line area 46 of about the same width extends lengthwise down the center of sheet 11 and divides the sheet 11 into the longitudinally extending first and second halves 40 and 40'.

In this manner, the border bands between the perforation zones are preferably minimized, and the first and second pairs of first, second and third zones occupy substantially the entire sheet 11. However, the border bands do prevent the elongated perforations of each zone from encroaching one another or reaching the edges of the sheet 11 to preserve sheet 11 integrity.

Figure 6:
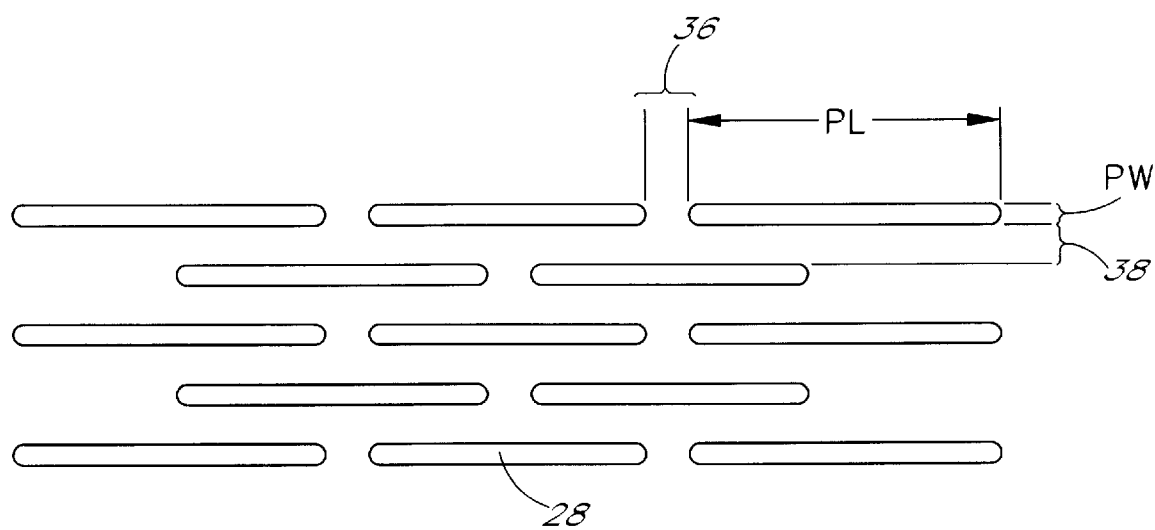
FIG. 6 is an enlargement of a portion of the sheet of FIG. 2, illustrating slot dimensions in accordance with one embodiment of the invention.

Turning to FIG. 6, one perforation pattern of a segment of the plurality of elongated perforations 28 of each zone is shown in enlarged detail. Each elongate perforation 28 is preferably about 3.0 mm in perforation length PL and between 0.10 mm and 0.25 mm in perforation width PW. The end to end and side to side separations 36 and 38 between adjacent perforations 28 is preferably about 0.3–0.4 mm in both cases. The perforations 28 are in parallel with directions 50, 52 and 54 in each of the perforation zones depicted in FIG. 2.

Figure 4:
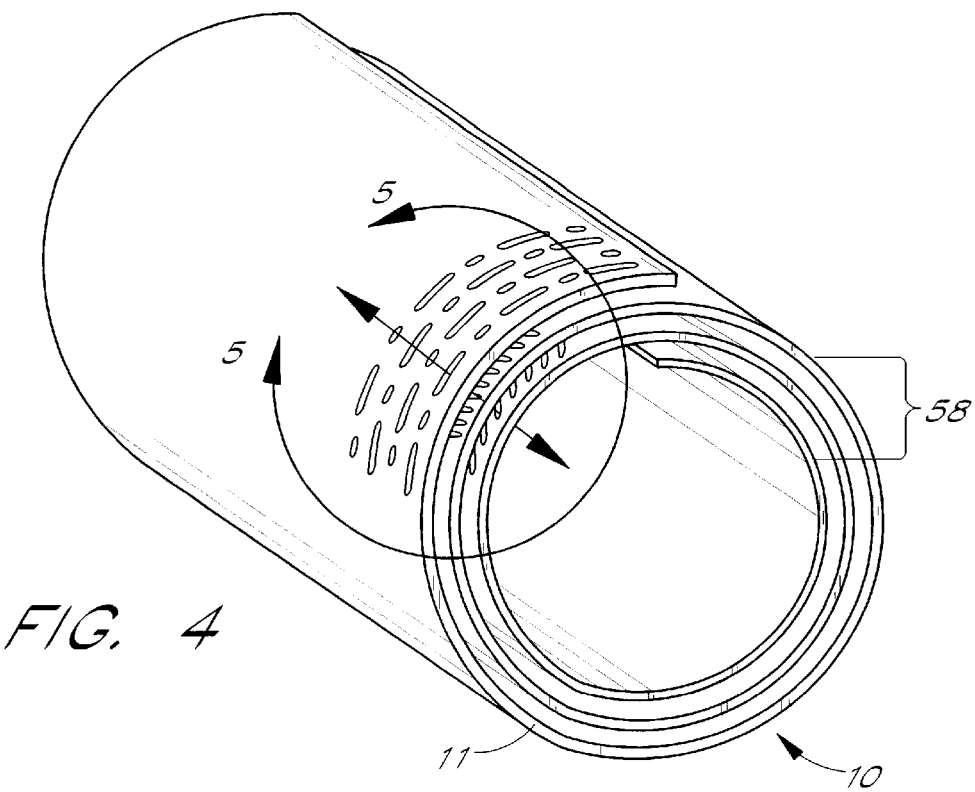
FIG. 4 is an enlarged perspective view of the sheet of FIG. 2 rolled up in a tubular body to form overlapping layers having overlapping zones of perforations.
Figure 5:
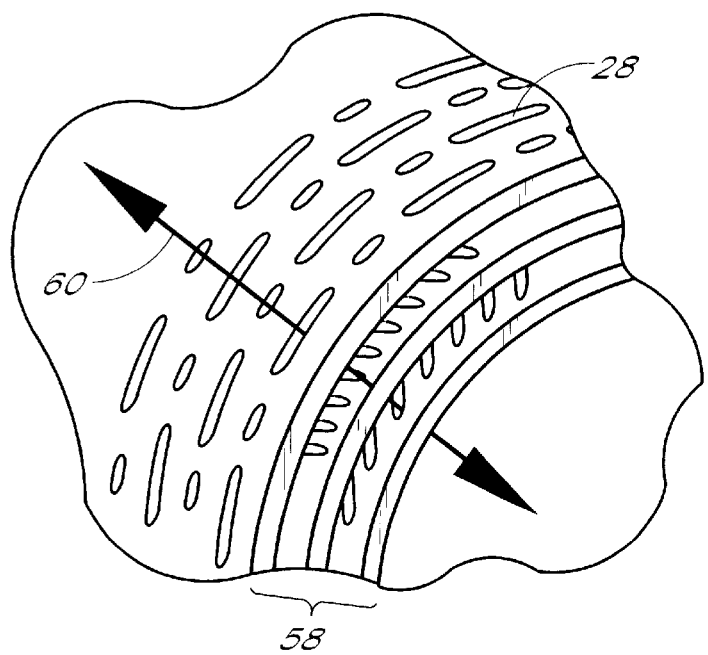
FIG. 5 is a fragmentary enlarged perspective view of a side wall section of three layers of the sheet of FIG. 2 rolled up to overlie one another and depicting alignment of the perforations in the first, second and third perforation zones to provide spaced apart, continuous openings through the side wall.

Turning to FIGS. 4 and 5, the stent 10 of the illustrated embodiment is depicted in one of the possible expanded roll state wherein the sheet 11 is rolled up in the sheet length direction SL in three overlapping rolled up sheet layers which together form the side wall 58 of tubular body 13. Consequently, the perforation zones 30, 32, and 34 in the first half 40 and 30', 32', 34' in the second half 40' overlap one another around most if not all of the perimeter of side wall 58. A portion of the perforations 28 in the overlapping zones 30', 32' and 34' are also depicted in FIGS. 4 and 5 to illustrate the formation and maintenance of openings, e.g., as opening 60, extending through the side wall 58. The alignment of the perforations 28 in each overlapping zone 30', 32', 34' and 30, 32, 34 provides a multiplicity of such spaced apart openings extending completely through the side wall. Given the dimensions and spacing of the perforations 28 stated above, each opening 60 is no greater in size than the perforation width PW. The spacings in the sheet length SL and sheet width SW directions between openings 60 is dependent on the number of layers formed when the sheet 11 is unrolled into the expanded roll state to fit into the vessel lumens.

The spaced apart openings 60 are formed due to the complementary interaction of the first direction 50 with the second and third directions 52 and 54 of the elongated perforations 28 in each overlapping zone. As is evident from FIGS. 4 and 5, the alignment of the zones in the sheet length direction SL and the sheet width direction SW is not critical to the formation of the openings 60. A lateral shift or twist in the rolled up tubular body 13 is tolerable as it still allows the openings 60 to form due to the interaction of the perforations 28 extending at the +45° and −45° directions 52 and 54 in the inner layers with the 0° direction 50 in the outermost layer. The likelihood of twisting is lessened by orienting the perforations 28 in each zone in the mirror image manner depicted in FIG. 2 but may occur to a slight extent.

Although FIGS. 4 and 5 show the tubular body 13 formed of three overlapping layers, it will be understood that the tubular body diameter may be increased or decreased, thereby decreasing or increasing, respectively, the number of overlapping layers, to accommodate a larger or smaller vessel lumen diameter. When the diameter is increased and the tubular body 13 is formed with two overlapping layers (at least in part), the openings 60 may need to be spaced closer together and be somewhat smaller than the openings 60 depicted in FIGS. 4 and 5. When the diameter is decreased to a point where more than three overlapping layers are formed at least in part, the openings 60 may also be spaced further apart and be somewhat larger in size.

In this regard, the preferred embodiment of the stent described above and depicted in the drawings is preferably dimensioned to be used in blood vessels having a diameter in which the tubular body 13 is accommodated having one and one half, one and three quarters, two, three, four or five or more and any fraction therebetween of overlapping layers in its expanded roll state. A selection of stents 10 may be provided with the sheet length SL and the lengths of the perforation zones 30, 32, 34 and 30', 32', 34' tailored to accommodate a particular range of body vessel lumen diameters. A selection of such stents may also be provided having different sheet widths SW to bridge vascular defects of differing lengths in the body vessel. The physician may select the appropriately dimensioned prosthesis 10 for the particular body vessel.

Preferably the second and third directions 52 and 54 are at +45° and −45°, respectively, to the 0° direction 50, and therefore extend to 90° to one another. These angels may also be varied as long as the perforations 28 extending at each angle overlie one another when the sheet 11 is rolled into the tubular body 13 and provide a suitable number of aligned openings 60 through the multiple layers of the side wall.

In the illustrated preferred embodiment, the perforation zones are arranged such that in the first half 40, the first, second and third zones 30, 32, 34 are arranged across the center line border band 46 from the second, first and third zones 30', 32', 34' of the second half 40', so that the second and third directions 52, 54 of the second and third zones 32, 32' and 34, 34' are adjacent to one another across the center border band 46 in order to balance twist biases induced in the sheet 11 by the second and third directions 52 and 54 of the elongated perforations 28. The particular order in which these zones appear from the outer-most to the inner-most layers forming the size wall of tubular body 13 may be changed from the order depicted in FIGS. 2–5. In any such configuration, the sheet 11 may be rolled up such that the first perforation zones 30, 30' are in the inner-most layer rather than the outer-most layer as shown.

Moreover, while the preferred number of perforation zones in each half is three to provide a substantially three layer, tubular body in the expanded roll state, only two or more than three such perforation zones may be provided in each half to provide substantially two or more layers in the tubular body. The case of four perforation zones in each half to provide substantially four layers in the tubular side wall in the expanded roll state, an additional pair of side by side perforation zones may be provided both having elongated perforations extending at 90° to the length direction 50 of the sheet.

In addition, the above-described preferred embodiment of the stent of the present invention is provided with perforation zones formed in portions of first and second halves of the sheet on either side of the center line area 46 to thereby form parallel rows of perforation zones along the sheet length SL. It is also contemplated that additional rows of parallel perforation zones may be formed across the sheet width SW and extending the sheet length SL. A selection of directions 50, 52, 54 (or other suitable directions) for each perforation zone is to be made to offset the above described curl bias forces induced by the perforation directions so that the tendency of the sheet to twist out of alignment with the sheet length direction or 0° direction 50 when in the expanded roll state is minimized.

Although the sheet is preferably formed of metal foil, the invention may be practiced using sheets formed of biocompatible plastic materials or other suitable sheet materials.

The prostheses of the present invention may be employed as a graft bridging an aneurysm in a blood vessel and may be employed in the system depicted in the above-referenced '906 application. The prostheses of the present invention may be used in any of a variety of alternative applications where radial support is desired or channeling of blood is desired. Repair of a tear in the intimal wall of an artery or a repair of a dissecting aneurysm is contemplated. The present invention may also be utilized as a stent, such as following radial expansion of a stenosis by balloon angioplasty, laser ablation, rotational atherectomy, or other lesion modifying technique.

Although the above described stent 10 is preferably self-expanding, it will be understood that the perforation zones and complementary pattern may also be used in multilayer sheet stents that are expanded by an expansion mechanism such as a balloon catheter from the collapsed roll state to an expanded roll state in order to provide the openings 60 through the side wall of the tubular body formed on expansion.

The perforation pattern of the present invention allows the resulting openings 60 to be relatively numerous and small enough to avoid significant blood loss therethrough. Although the present invention has been described in terms of certain particular aperture patterns, any of a wide variety of aperture size, shape and distribution patterns can be utilized and still accomplish the functional advantages of the present invention. In general, the aperture size and pattern should seek to produce a net aperture through the side wall of the prosthesis which is small enough to prevent substantial blood loss therethrough, and large enough to facilitate endothelial cell growth.

By "net aperture" opening, it is meant the effective cross section of the aperture which has a clear or tortuous passageway through each of the two or three or four or five or more adjacent layers of the sheet when rolled up into the expanded, implanted diameter. Thus, for example, referring to FIG. 5, each slot in each of the three adjacent layers may have a width of about 0.2 mm and a length of about 3 mm. Due to the misalignment of the longitudinal axis of the overlaying apertures, the net opening 60 through the side wall 58 will be on the order of about 0.2 mm in diameter.

In general, net aperture openings of less than about 0.5 mm, preferably less than about 0.25 mm and more preferably less than about 0.10 mm are contemplated. Net aperture openings of about 0.05 mm or smaller may be preferred in some applications. The net aperture opening and aperture density preferably produce a blood or blood serum flow rate through the side wall within the range of from about 100 to about 3000 $cc/cm^2$/minute. More preferably, the leak rate is less than about 300 and preferably no more than about 250 $cc/cm^2$/minute.

Net aperture dimensions much greater than the recited ranges may also work, but may delay the time until the apertures are sealed off by natural mechanisms. This may be undesirable in an application intended for use as a vascular graft, in which excessive blood loss through the wall of the aperture may be undesirable. In addition, the net aperture distribution should be such that will permit a continuous or substantially continuous layer of endothelial cell growth along the wall of the prosthesis. At the present time, it is believed that the endothelial cell growth will travel no more than about 0.125 inches along a metal continuous surface.

As recited supra., the minimum aperture size should be sufficient to permit endothelial cell growth therethrough. This may be accomplished in apertures having a net cross section measured in microns, with exact limits which can be established through routine experimentation by those of skill in the art. Thus, one hole pattern and distribution pattern for a porous sheet could involve the use of a laser perforation or other technique for producing hundreds or thousands or more of apertures per square centimeter. Distribution may be regular or random, as long as there exists a statistical likelihood that a continuous aperture 60 will extend through each of the adjacent wall layers in the expanded, implanted diameter, at a distance of no further apart than about ⅛ or ¹⁄₁₀ of an inch as has been discussed.

One advantage of the aperture configuration and patterns illustrated in FIG. 2, and other pattern designs not specifically illustrated but contemplated herein, is that an appropriate net aperture size will be achieved in the rolled implanted expanded prosthesis, throughout any of a variety of implanted diameters. Since the same stent or graft will optimally be useful in any of a range of vessel diameters, the optimal aperture pattern and distribution will permit the stent to expand from the insertion diameter to any of a variety of implanted diameters which will always achieve a net aperture distribution and dimension in accordance with the foregoing. Thus, the prothesis of the present invention is expandable from an insertion diameter to any of a variety of implanted diameters and still achieve the endothelial cell growth objectives of the present invention.

As will be appreciated by those of skill in the art in view of the disclosure herein, the embodiments which utilize zones of longitudinal slots may be provided with any of a variety of orientations with respect to each other. One consequence of certain aperture patterns is the introduction of roll bias in the final product. By roll bias, it is meant the tendency of the stent upon unwinding from the insertion diameter to the implanted diameter to unwind in a manner that spirals out in an axial direction, thereby extending the axial length of the stent. In applications where a roll bias is undesirable, perforation patterns, such as left- and right-hand mirror image patterns, have been found to assist in minimizing roll bias.

For example, although the orientation of the longitudinal slots in the multi-zone embodiment of FIG. 2 are 0° from the longitudinal axis, −45° and +45°, all longitudinal slots may alternatively be provided with the same orientation throughout the sheet. Preferably, to minimize roll bias, at least one zone or a group of zones will have an orientation of −θ to create a first roll bias, and an equivalent zone or groups of zones will have an orientation of +θ, with respect to the longitudinal axis of the sheet to create an opposite roll bias. θ may range from about 10° to about 80°, preferably from about 30° to about 60°, and more preferably from about 40° to about 50° with respect to the longitudinal axis of the sheet. Alternatively, one or more groups of apertures may comprise oval or round holes, rectangular openings, or other geometric configurations, provided that the net aperture size and distribution in the wall of the finished stent when in the intended expanded diameter satisfies the functional requirements described above.

The apertures may be provided in any of a variety of manners which will be understood to those of skill in the art. For example, a sheet of material, such as Elgiloy, or any of a variety of stainless steel or other biocompatible materials having a sufficient spring force is provided. The sheet may then be laser etched, photo etched, perforated using electronic discharge technology or other means, depending upon the sheet thickness, physical properties of the alloy or polymer sheet and desired aperture diameters and patterns. In one embodiment of the invention, the apertures are produced using conventional photo etching technology. The etched sheet is then rolled up and restrained within about a 2½ cm restraining tube, and heated to approximately 900° F. for approximately 4 hours, to relieve stress. In general, the larger the diameter of the restraining tube during the heat stress relief step, the greater the spring force in the finished prosthesis. The heat treated prosthesis may then be tightly rolled and installed within a deployment catheter, or packaged for other use at the clinical site. Prior to loading or packaging, coatings may be added to the tubular prosthesis. Anticoagulants, such as heparin, endothelial cell growth initiators, macrophage inflammation inhibitors or any of a variety of other drugs or coatings, may be utilized, as will be apparent to those of skill in the art in view of the disclosure herein.

Another feature of the prevent invention is the provision of an extremely low leading edge profile in the implanted prosthesis. The leading edge profile, or radial thickness of a prosthesis wall, as seen in a direction of blood flow, is believed to cause undesirable turbulence in the bloodstream. One conventional coronary artery stent, for example, has a leading edge profile on the order of 0.007 inches. The spiral rolled construction of the present invention permits the use of very thin sheet material, which provides a relatively high hoop strength for resistance to radial compression, as a function of total wall thickness. This allows blood flow turbulence to be minimized.

For example, in a stent having a sheet thickness of about 0.0015, rolled up to have three overlapping layers and a net wall thickness of about 0.0045 in accordance with the present invention, is expected to have a hoop strength in excess of that for conventional non-rolled stents or grafts having a greater wall thickness. In general, radial deformation preferably begins within the range of from about 50 to about 750 mm Hg global radial pressure. Sheet thicknesses as low as 0.001 inches, and preferably as low as 0.0005 or less (to produce a leading edge profile of 0.0015 inches or less in a three layer as implanted prosthesis) are contemplated by the present inventor.

In accordance with an alternate embodiment of the present invention, the leading edge profile can be reduced by staggering the axial ends of the layers of the tubular stent. Thus, when the stent is rolled up into its normal expanded configuration within the vessel, each internal rolled layer is slightly inset from the previous layer thereby creating a stepped path for the blood interface rather than the full frontal face of several layers stacked on top of each other. This can be accomplished several different ways, as will be apparent to those of skill in the art in view of the disclosure herein. For example, tapering the unrolled sheet width such that it does not correspond to a regular rectangle can produce a stair step leading edge when in the rolled configuration. Alternatively, the sheet can be predisposed to roll into a slight telescoping configuration, thereby achieving a stepped leading edge profile.

Thus, for a three layer stent constructed from a sheet having a thickness of 0.001 inches, the leading edge profile can be reduced from 0.003 inches in a nonstepped configuration to three separate 0.001 inch steps. Each step can be axially spaced apart from the other step by any amount determined clinically desirable, such as within the range of from about 0.001 inches to about 0.01 inches or more. The axial run between adjacent steps can be optimized to produce the least turbulent leading edge profile, yet not adversely affect the structural integrity (e.g. radial strength) of the stent, as can be determined through routine experimentation by one of skill in the art in view of the particular application for the stent.

In addition, the tubular prosthesis of the present invention provides a relatively uniform leading edge. Many alternate stents and grafts have a jagged or angular leading edge, as a consequence of the wire construction or diamond patterns that may be cut into the wall of the prosthesis. The uniform leading edge is also believed to assist in minimizing leading edge turbulence. Blood flow turbulence may also be minimized, and compatibility of the prosthesis is optimized by the microporous apertures of the present invention, particularly when provided in a density and distribution as discussed above. The facilitation of a continuous endothelia cell coat along the interior wall of the stent is believed to make the stent appear to the blood and surrounding tissue more biocompatible than the material of the stent may otherwise appear to be.

In accordance with another aspect of the present invention, there is provided a method and apparatus for treating a site in a body lumen by deploying a plurality of tubular supports or stents sequentially along the length of a treatment site. Thus, two or more stents can be positioned sequentially one after another directly against the vessel wall, or within a tubular graft as will be discussed in greater detail below.

Multiple sequential stenting in accordance with the present invention can provide a variety of advantages over conventional stenting techniques. For example, although many coronary artery lesions are relatively short (e.g., 1 cm), other vascular treatment sites may be as long as 5 or 10 cm or longer. Conventional balloon expandable stents are normally deployed using a single stent or single articulated stent per balloon catheter. Thus, where multiple stent treatment is desired, a number of separate balloon catheter entries must normally be used. Although longer stents may result in less total number of stents for a given axial treatment length, long stents may be difficult or impossible to navigate through tortuous and/or narrow vasculature. Even with a long stent, the fixed stent length limits clinical judgment. In addition, most or all practical stent designs or articulated stent segments tend to assume a generally linear configuration once deployed and expanded in a vessel. Thus, the expanded stent tends to straighten the vessel which may prevent stenting of lesions located in curved portions of the vessel. In addition, even in a relatively straight vessel, the linear nature of conventional expanded stents produces a risk of injury at the junction between the axial ends of the stent and the vessel wall.

Thus, in accordance with the present invention, a plurality of relatively short tubular stents are deployed one after another along a treatment length of a vessel. The axial length of each stent may be varied depending upon the desired clinical application. For example, in a coronary artery application, multiple stents may each have an axial length of within the range of from about 0.25 cm to about 2 or 3 cm or longer. Although shorter stents may be used in some applications, stents having an aspect ratio of at least about one and often two or more may be desirable. The aspect ratio is the ratio of the length of the stent to the diameter in the expanded configuration, such that a 16 mm axial length stent positioned within an 8 mm diameter vessel exhibits an aspect ratio of two to one. Stents for use in the present aspect of the invention may be but are not necessarily provided with the various aperture patterns disclosed previously herein for, among other purposes, minimizing roll bias. Thus, relatively higher aspect ratios may be desired in tubular stents which have not been patterned to minimize roll bias.

In general, the number of stents delivered in a single procedure at a treatment site will be a function of the length of the treatment site, the length of the individual stents, and the spacing selected by the clinician between adjacent stents. In general, relatively shorter axial length per stent may be desirable if the treatment site is in a relatively curved portion of the vessel, as will be discussed.

Referring to FIG. 7, there is illustrated a schematic cross-sectional view of a multiple stent deployment catheter 120 in accordance with the present aspect of the invention. The deployment catheter 120 comprises a proximal end 122, a distal end 124 and an elongate flexible tubular body 126. In general, a control 128 is provided on the proximal end 122 for manipulating the catheter 120 and controllably deploying one or more tubular stents 130. The stents are illustrated as spaced apart for clarity, but would normally be in axial contact with each other within the delivery catheter.

In general, the elongate flexible tubular body 126 will have an outside diameter within the range of from about 1 mm to about 8 mm and at least one central lumen 132 having an inside diameter within the range from about 0.67 mm to about 7.5 mm. Any of a variety of conventional materials and techniques can be used for producing tubular body 126, as are well known in the catheter construction arts. In general, for coronary artery applications, the tubular body 126 will have an axial length within the range of from about 135 cm to about 175 cm. For peripheral applications, the length of the tubular body will depend upon the distance between the percutaneous or surgical access site and the treatment site. For example, in a femoral-popliteal graft application, the length of tubular body 126 will generally be within the range of from about 50 cm to about 120 cm, and the outside diameter will range from about 1 mm to about 8 mm.

One, and preferably two or more stents 130 are positioned within the distal end of lumen 132. The stents 130 are preferably "self-expanding" such that they are maintained in a relatively small diameter configuration inside of lumen 132 but they expand radially outwardly when released from the catheter. Any of a variety of known self-expanding stents can be used, including spring coil, shape memory metal (e.g., Nitinol) as will be apparent to those of skill in the art. Preferably, however, a rolled flexible sheet type stent will be used.

In one embodiment of the invention, the catheter 120 is preloaded with the desired number of stents 130 either at the point of manufacture, or at the clinical site, prior to positioning within the patient. For example, two, three, four, five, six, seven, eight, nine, or as many as ten or more stents 130 can be positioned within the catheter 120 prior to insertion into the patient.

In one embodiment of the catheter 120, the stents 130 are loaded in a proximal direction into the distal end of the lumen 132. The total number of stents 130 for a given catheter design will depend upon the desired number of stents available for delivery (the clinician may choose not to use all stents loaded within the catheter 120) as well as engineering reasons such as the coefficient of static friction between the stents 130 and the interior wall of lumen 132. In embodiments intended to carry a relatively large number of stents 130, a lubricous coating such as teflon or paralene or others known in the art may desirably be provided on the interior wall of the lumen 132 as well as on the outside surface of each stent 130.

In an alternate embodiment, the lumen 132 has a substantially constant interior diameter throughout the entire axial length of the catheter 120. In this embodiment, the stents 130 can be "breach" loaded into the proximal end of the catheter 120. A pusher may then be utilized to advance the stents either one at a time or as a group distally through the lumen 132 into a deployment zone within the distal end of the catheter 120. For breach loading designs of catheter 120, additional stents 130 may be loaded into the catheter 120 while the catheter remains within the patient. For this purpose, the pusher is proximally withdrawn from the catheter, and additional stents as desired may be loaded into the proximal end of the catheter and advanced distally to the deployment zone. At that point, the catheter is positioned precisely by the clinician and the additional stent or stents may be deployed as desired.

For either the distally loaded stent or particularly the proximal loaded stent embodiments, it may be desirable to seek to minimize friction between the stent and the interior wall of lumen 132. For example, lubricous coatings such as those identified before can be used.

In addition, it may be desirable to rotate the stent within lumen 32, as the stent travels axially through the catheter. From the direction illustrated in FIG. 7a, rotation of the stent 130 is preferably accomplished in a clockwise direction so that the radially outward most edge of the stent 130 trails against the interior wall of the lumen. In this manner, the stent tends to wind more tightly, and friction between the stent and catheter is reduced. Rotation can be accomplished by rotating the core 136, and frictionally engaging the pusher 134 with the stent. Any of a variety of structures for imparting a rotation to the stent 130 can be readily envisioned by one of skill in the art in view of the disclosure herein.

The stents 130 are positioned distally of a deployment surface such as the distal surface of a pusher 134 for advancing the stents 130 distally out of the end of the catheter 120. The pusher 134 is generally connected to or is the distal end of an elongate flexible axial force transmitting structure such as a central core or tubular body 136 which extends proximally throughout the length of the catheter.

Distal advancement of tubular body 136 with respect to the catheter 120 will deploy stents 130 from the distal end of the catheter 120 as will be apparent to those of skill in the art in view of the disclosure herein. In a preferred deployment method, the relative movement between the catheter 120 and core 136 is accomplished by holding the core 136 in an axially fixed position and retracting the catheter proximally until a stent 130 is deployed. Thus, the distal end of the catheter is positioned at the desired location for the distal end of the implanted stent prior to stent deployment.

Alternatively, the tubular body 136 may be replaced by a nontubular push wire, which runs in parallel to the guidewire 138. In an embodiment using a tubular support 136, the guidewire 138 preferably runs axially through a central lumen in tube 136, through pusher 134 and axially through the stents 130.

Preferably, the proximal end of the catheter 122 is provided with a control 128 for controllably deploying the stents 130. Preferably, the control 128 comprises a structure for indexed deployment of the stents 130, such that one stent may be deployed at a time and under the direct control of the clinician. For example, control 128 may comprise a handle 140 and an actuator 142 such as a lever or trigger coupled to a rachet structure 144. The trigger 142 and rachet 144 may be calibrated such that a single pull of the trigger 142 deploys a single stent 130. In this manner, the clinician can deploy the stents 130 sequentially while proximally withdrawing the catheter 120 to produce a series of axially adjacent deployed stents.

Alternatively, the tubular body 136 can be provided with a plurality of visual indicia such as index lines, which are visible to the clinician on the proximal end of the catheter 120. The clinician can manually advance the pusher 134 distally with respect to the proximal end 122 of the catheter 120 to deploy stents 130 as desired. Any of a wide variety of alternate deployment control structures can be readily designed, as will be apparent to those of skill in the art in view of the disclosure herein.

Referring to FIG. 8, there is illustrated a plurality of stents 130 deployed serially in a curved portion of an artery 146. The number of stents 130 used to treat a given axial length treatment site is largely within the judgment of the clinician, depending upon lesion morphology and other considerations. For example, a lesion or other treatment site having an axial length of about 12 cm to 14 cm may be treated using five 2 cm stents having a space between stents within the range of from about 0.1 cm to 1 cm. The spacing between adjacent stents can be varied considerably depending upon clinical judgment. In addition, the present invention permits the spacing of adjacent stents in a manner that prevents occlusion of branch arteries such as branch artery 148 illustrated in FIG. 8.

Referring to FIG. 9, there is disclosed one embodiment of a tubular graft and deployment catheter 160 such as might be used for a transluminal grafting procedure. The catheter 160 generally comprises an elongate flexible tubular body 162 having a proximal end 164 and a distal end 166. Proximal end 164 is provided with a manifold 168 containing appropriate connectors as may be desired in view of the functionality of the catheter 160. For example, an access port 169 is preferably axially aligned with the catheter 160 as is known in the art for receiving a guidewire 182. Access port 169 is also provided with a stent deployment actuator 178, which may be manipulated to deploy stent 172 from the distal end 166 of the catheter 160. Deployment actuator 178 may comprise a plate 180 such as a radially outwardly extending annular flange attached to a push wire or tube 181. In one embodiment, the distal surface on plate 180 is spaced proximally of the access port 169 by a sufficient distance that advancing plate 180 distally into contact with port 169 provides sufficient travel to deploy a single stent 172 from the distal end of the catheter. Preferably, actuator 178 is provided with a lumen (not illustrated) to accommodate guidewire 182. Additional access ports such as dye port 171 may also be provided as desired.

In general, the distal end 166 of the catheter 160 is provided with a stent 172 and a flexible tubular graft 176. Preferably, the stent 172 is connected to the graft 176, either at a point beyond the distal end of the tubular body 162 or through one or more side openings on the tubular body 162.

The distal end 166 in the illustrated embodiment is provided with an axially extending slot 170. Slot 170 permits the rolled stent 172 to be positioned within the distal end of the tubular body 162 with a free end 174 of the rolled stent 172 extending through the slot 170. In this manner, the stent 172 can be positioned fully within the catheter 162, and be connected to a graft 176. The graft 176 is connected at its distal end to the free end 174 such as through the use of any of a variety of adhesives, stitching, thermo-bonding, mechanical interfit, or the like. The vascular graft 176 trails proximally along the outside of tubular body 162. Grafts 176 having lengths within the range of from about 2 cm to about 30 cm are contemplated, although other lengths may be desirable depending upon the clinical application. Any of a wide variety of known graft materials, such as dacron or polytetrafluoroethylene, may be utilized, together with any subsequently developed graft materials as will be apparent to those of skill in the art.

Referring to FIG. 11, there is disclosed one embodiment of a distal end for a stent deployment catheter, which can be adapted for use on either the catheter design of FIG. 7 or FIG. 9 above. A generally cylindrical tip 200 is provided with a proximally extending annular flange 202, adapted to fit within the tubular body 162. Proximal flange 202 terminates at its proximal end in a stop surface 204. Stop surface 204 is spaced axially apart from a complimentary stop surface 208 on the axially moveable actuator 206. A guidewire lumen 207 is illustrated extending axially through the actuator 206.

A stent compartment 210 is disposed distally of the actuator 206. As will be apparent to those of skill in the art, the axial length of stent compartment 210 will be a function of the number of stents desirably loaded therein. Similarly, the axial space between stop surface 204 and complimentary stop surface 208 will correspond to the desired axial travel of the actuator 206 to fully deploy the stents contained in stent compartment 210. Any of a wide variety of other specific structures can readily be devised for deploying self-expanding stents from the distal end of catheter 164, 120 as will be apparent to those who have skill in the art in view of the disclosure herein.

In use, a surgical incision or percutaneous puncture is made to provide access to a vessel to be treated. The catheter 162 is thereafter inserted into the vessel and advanced transluminally until the stent 172 is positioned at or beyond the treatment zone from the perspective of the catheter 162. The deployment structure is advanced distally with respect to the catheter 162, so that the stent 172 is deployed from the distal end of the catheter 162. Deployment of the stent 172 from the catheter 162 permits the stent 172 to assume its enlarged radial configuration within the vessel, thereby supporting the tubular graft 176 against the vessel wall. The catheter 162 may thereafter be proximally withdrawn, leaving the graft 176 extending from the stent 172 towards the clinician through the artery or other vessel.

The proximal end of the graft 176 may be secured such as through a surgical attachment procedure as is known in the art. Alternatively, the proximal end 176 may be secured within the vessel through the use of a second expandable stent deployed from the same catheter 162 or a separately introduced catheter. In a preferred embodiment, the catheter 162 contains at least the distal stent 172 and a proximal stent (not illustrated) for supporting the proximal end of the graft 176. Thus, a procedure such as a femoral-popliteal bypass can be accomplished percutaneously in accordance with the present invention without the need for a surgical cutdown and anastomosis.

Figure 12:
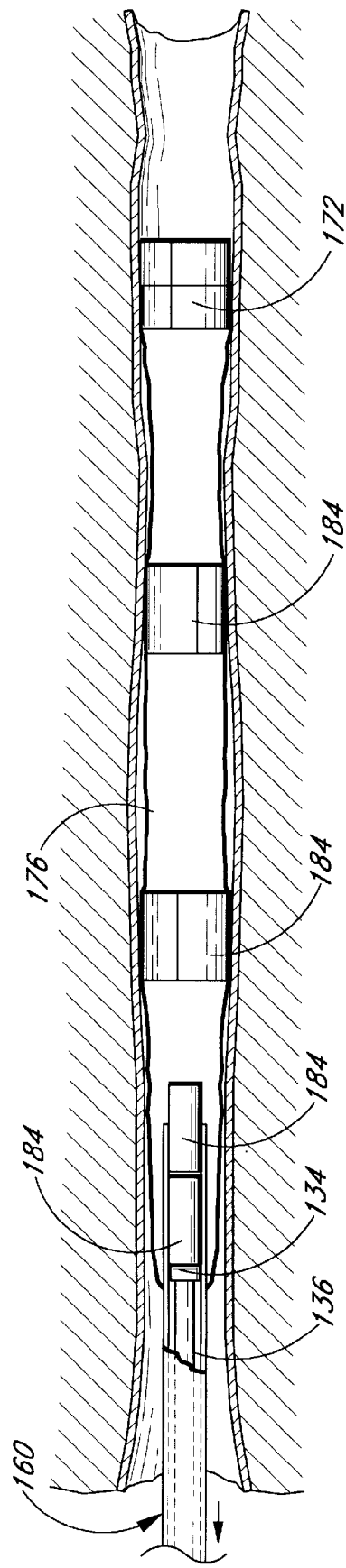
FIG. 12 is a cross-sectional schematic view showing a plurality of tubular supports being positioned within a graft in a body vessel.

In a further embodiment, as illustrated mid-procedure in FIG. 12, the catheter 162 is provided with three or more stents, including the distal stent 172 and two or more additional self-expanding stents. In this manner, the catheter can be withdrawn proximally following placement of the distal stent 172, and one or more stents can be positioned at intermediate locations between the proximal and distal ends of the graft 176. A proximal most stent can be deployed at or about the proximal end of the graft 176. In this manner, a plurality of supports can be positioned within a vascular graft, for providing intermediate support thereby enhancing patency of the graft along its entire length.

The multiply supported graft aspect of the present invention can be accomplished in a variety of ways, depending upon catheter design and clinical preference for a given procedure. For example, the distal stent 172 may be attached to the graft 176 as has been discussed. One or more intermediate supports 184 may also be attached to the graft 176, such as by axially elongating the slot 170 in a proximal direction on catheter 160, as will be apparent in view of the disclosure herein. This design ensures a predetermined spacing between axially adjacent intermediate supports 184 and distal end supports.

Alternatively, the axially spacing between adjacent supports is determined by the clinician during the procedure. In this application, the intermediate supports 184 are positioned within the catheter 160 in a manner described in connection with the catheter of FIG. 7. Thus, axial distal displacement of a stent deployment surface 134 with respect to the catheter 160 controllably deploys the intermediate stents 184.

Depending upon the length of the graft 176 and the spacing between adjacent supports, the clinician may or may not utilize all of the intermediate supports 184 in a given graft implantation. One of the supports 184 will preferably be positioned at or near the proximal end of the graft 176, and will thus become the proximal attachment point of the graft.

In a relatively large vessel procedure, such as a femoral-popliteal bypass, the outside diameter of the catheter 160 is about 2–3 mm and the inside lumenal diameter of an expanded stent 184 will be on the order of about 4–10 mm.

Thus, it may be possible for the physician to advance the catheter 160 distally through a previously implanted stent 184 to deploy additional intermediate stents 184 if the physician determines during the procedure that the spacing between adjacent stents 184 was undesirably large. Fluoroscopic or other visualization of the procedure in real time will permit the clinician to deploy a first number of supports 184, evaluate the resulting patency of the lumen, and, if desired, deploy a second support or set of supports 184 as may appear warranted in view of the visualization of the patency of the graft lumen.

Proximal retraction of the catheter 160 following deployment of the distal stent 172 may cause a proximal motion of the graft 176 within the vessel. It may thus be desirable to anchor the distal stent 172 to the vessel wall or otherwise increase the coefficient of static friction between the stent 172 and the vessel wall. Although providing the stent 172 with a relatively larger radially outwardly directed expansion force may accomplish a sufficient anchoring of the stent 172 in the vessel, excess outward force may be medically undesirable.

Figure 13:
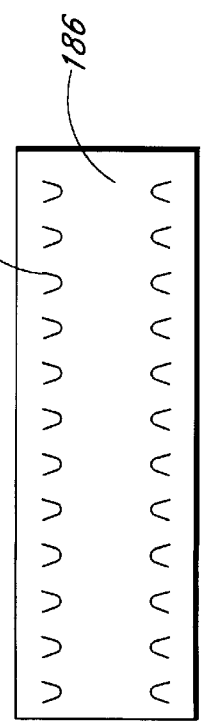
FIG. 13 illustrates an unrolled tubular support of the present invention having a plurality of proximal and distal anchors thereon.

As an alternative anchoring structure, the distal stent 172 and possibly also the intermediate and proximal stents 184 may be provided with a plurality of anchors. Referring to FIG. 13, there is illustrated a flat sheet 186 from which the tubular stents 172 and 184 may be wrapped. The sheet 186 is provided with a plurality of slots or punch-outs 188 throughout at least a portion of the axial length of the sheet 186. Due to the rolled configuration of the sheet (see FIG. 14) in the as-used orientation, in which two or three or more overlapping layers of the sheet 186 will normally be present, anchors 188 need not be provided throughout the axial length of the sheet 186.

Figure 14:
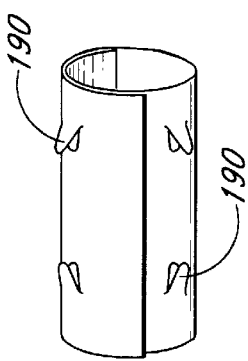
FIG. 14 is a perspective view of the sheet of FIG. 13 rolled into the form of a tubular support.

When the stent is rolled as shown in FIG. 14, the punch-outs 188 will tend to produce a radially outwardly inclined ramp 190 which can be used to anchor the graft 176 against the vessel wall.

Although the present invention has been described in terms of certain preferred embodiments, variations of the invention will become apparent to those of skill in the art in view of the disclosure herein. Accordingly, the scope of the invention is intended to be limited solely by the attached claims, and not by specific structural recitations contained herein.

What is claimed is:

1. An endobypass delivery system, comprising:
   an elongate, flexible, tubular body, having a sidewall and proximal and distal ends;
   a support cavity in the tubular body, accessible through both an end opening on the distal end of the tubular body and through a side opening in the sidewall of the tubular body;
   a first self-expanding support in the support cavity, the support having a free edge extending through the side opening; and
   a tubular graft attached to the free edge.

2. An endobypass delivery system as in claim 1, wherein the self-expanding support comprises a flexible sheet rolled into a tubular configuration.

3. An endobypass delivery system as in claim 1, further comprising an elongate flexible deployment column extending axially through the tubular body, for deploying the self-expanding support.

4. An endobypass delivery system as in claim 3, wherein the support further comprises a central lumen for slidably receiving a guidewire therethrough.

5. An endobypass delivery system as in claim 1, wherein the tubular graft has an axial length within the range of from about 75 cm to about 175 cm.

6. An endobypass delivery system as in claim 1, further comprising a second self-expanding support in the support cavity, positioned proximally of the first self-expanding support.

7. An endobypass delivery system as in claim 6, further comprising at least a third self-expanding support in the support cavity, disposed proximally of the second self-expanding support.

8. An intravascular graft delivery catheter, comprising:
   an elongate, flexible tubular body;
   a self-expanding graft support, removably positioned within the tubular body, wherein said self-expanding graft support comprises a flexible sheet, rolled into a generally cylindrical configuration and a distal portion of the tubular body is provided with an axially extending slot, and a free end of the rolled sheet is connected through the slot to the graft; and
   an elongate, flexible tubular graft, secured to the support and extending proximally along the tubular body.

9. The intravascular graft delivery catheter as in claim 8, wherein the catheter extends axially through a central lumen in the tubular graft.

10. An intravascular graft delivery catheter as in claim 8, further comprising an outer introduction sheath, for surrounding the tubular graft.

11. An intravascular graft delivery catheter as in claim 8, further comprising at least a second graft support positioned within the tubular body.

12. An intravascular graft delivery catheter as in claim 8, further comprising an axially movable deployment structure for deploying the graft support from the distal end of the tubular body.

13. An intravascular graft delivery catheter as in claim 12, wherein the axially movable deployment structure comprises an elongate flexible tube.

14. An intravascular graft delivery catheter as in claim 12, further comprising a proximal control for distally advancing the deployment structure for deploying the graft support.

15. An intravascular graft delivery catheter as in claim 8, wherein the graft extends proximally from the graft support within the tubular body.

16. An intravascular graft delivery catheter, comprising:
   an elongate, flexible tubular body;
   a self-expanding graft support, removably positioned within the tubular body; and
   an elongate, flexible tubular graft, secured to the support and extending proximally along the tubular body, wherein the graft support comprises a flexible sheet, rolled into a generally cylindrical configuration, a distal portion of the tubular body is provided with an axially-extending slot, and a free end of the rolled sheet is connected through the slot to the graft.

17. An intravascular graft delivery catheter as in claim 16, wherein the catheter extends axially through a central lumen in the tubular graft.

18. An intravascular graft delivery catheter as in claim 16, further comprising an outer introduction sheath, for surrounding the tubular graft.

19. An intravascular graft delivery catheter as in claim 16, further comprising at least a second graft support positioned within the tubular body.

20. An intravascular graft delivery catheter as in claim 16, further comprising an axially-movable deployment structure for deploying the graft support from the distal end of the tubular body.

21. An intravascular graft delivery catheter as in claim 20, wherein the axially-movable deployment structure comprises an elongate flexible tube.

22. An intravascular graft delivery catheter as in claim 20, further comprising a proximal control for distally advancing the deployment structure for deploying the graft support.

23. An intravascular graft delivery catheter as in claim 16, wherein the graft extends proximally from the graft support within the tubular body.

* * * * *